United States Patent [19]

Paré

[11] Patent Number: 5,377,426
[45] Date of Patent: Jan. 3, 1995

[54] MICROWAVE-ASSISTED GENERATION OF VOLATILES, OF SUPERCRITICAL FLUID, AND APPARATUS THEREFOR

[75] Inventor: J. R. Jocelyn Paré, Gloucester, Canada

[73] Assignee: Her Majesty the Queen in right of Canada, as represented by the Minister of the Environment, Ontario, Canada

[21] Appl. No.: 12,475

[22] Filed: Feb. 2, 1993

[30] Foreign Application Priority Data

Feb. 10, 1992 [CA] Canada .................................. 2060931

[51] Int. Cl.$^6$ .............................................. F26B 3/34
[52] U.S. Cl. ............................................. 34/259; 34/82; 34/74; 219/690; 422/281
[58] Field of Search .................................. 34/1 P, 73–77, 34/79, 80, 82, 89, 78, 259, 263, 264, 265; 219/10.55 M, 10.55 R, 10.55A–10.55 F; 55/270; 422/281, 280

[56] References Cited

U.S. PATENT DOCUMENTS

| | | | |
|---|---|---|---|
| 2,064,422 | 12/1936 | Fenske et al. | 422/281 |
| 2,505,139 | 4/1950 | Pascal | 23/270 |
| 2,925,328 | 2/1960 | Romagnan | 23/267 |
| 3,409,447 | 11/1968 | Jeppson | 99/221 |
| 3,706,631 | 12/1972 | Falk | 195/1.8 |
| 4,168,418 | 9/1979 | Bird | 219/10.55 A |
| 4,221,680 | 9/1980 | Hardwick et al. | 34/1 P |
| 4,294,858 | 10/1981 | Moule | 426/241 |
| 4,400,398 | 8/1983 | Coenen et al. | 426/429 |
| 4,464,402 | 8/1984 | Gannon | 426/242 |
| 4,480,993 | 11/1984 | Guiriec | 432/266 |
| 4,554,132 | 11/1985 | Collins | 422/68 |
| 4,673,560 | 6/1987 | Masse et al. | 423/532 |
| 4,694,133 | 9/1987 | Le Viet | 219/10.55 M |
| 4,808,782 | 2/1989 | Nakagawa et al. | 219/10.55 M |
| 4,839,142 | 6/1989 | Charm | 422/21 |
| 4,898,673 | 2/1990 | Rice et al. | 210/634 |
| 4,929,462 | 5/1990 | Moorman et al. | 426/478 |
| 5,002,784 | 3/1991 | Paré et al. | 426/241 |
| 5,003,143 | 3/1991 | Marks et al. | 34/1 P |
| 5,026,565 | 6/1991 | McLachlan et al. | 426/241 |

FOREIGN PATENT DOCUMENTS

| | | |
|---|---|---|
| 47902/85 | 10/1986 | Australia . |
| 2026103 | 3/1992 | Canada . |
| 1209675 | 10/1970 | United Kingdom . |
| 2004197 | 3/1979 | United Kingdom . |

OTHER PUBLICATIONS

Katalin Ganzler and Andras Salgo Article entitled "Microwave Extraction–A New Method Superseding Traditional Soxhlet Extraction"–Sep. 8, 1986.
Journal of Chromatography 371 (1986) 299 306 "Microwave Extraction–A Novel Sample Preparation Method for Chromatography".
Flavour and Fragrance Journal–vol. 4, 43–44 (1989) "Microwave Oven Extraction of an Essential Oil".
Article entitled "Essential Oils and Microwaves" (original French document together with translation thereof).

*Primary Examiner*—Denise L. Gromada
*Attorney, Agent, or Firm*—McFadden, Fincham

[57] ABSTRACT

The generation of volatiles from liquid or solid materials is enhanced and accelerated by exposure to microwave radiation. Normally the energy transfer is effected preferentially toward the liquid or solid materials over the generated gaseous volatiles. Sufficient energy is provided at a selected rate that enhances the generation of volatiles to produce headspace samples. Alternatively, the rate can be selected so as to disrupt the equilibrium normally present between the liquid or solid phase and the gaseous phase and produce purge and trap samples; the latter process resulting from the selective energy transfer toward the liquid or solid phase over the gaseous phase. The rate of energy transfer can be chosen so as to bring the medium being subjected to microwave radiation to its supercritical state. The material having reached that state can further be used in numerous applications such as supercritical fluid extraction.

17 Claims, 2 Drawing Sheets

MICROWAVE-ASSISTED GENERATION OF VOLATILES, OF SUPERCRITICAL FLUID, AND APPARATUS THEREFOR

FIELD OF THE INVENTION

This invention relates to a method of generating volatile compounds from a variety of matrices containing volatilizable compounds therein. More particularly, this invention relates to a method and apparatus for the generation of volatile materials which can be achieved in a greatly reduced time frame as compared with conventional volatile expression or generation techniques.

BACKGROUND OF THE INVENTION

Grains containing fats and oils have been dried by microwave heating followed by steps to remove husks and to extract oils, as indicated in U.S. Pat. No. 4,464,402, Aug. 7, 1984 (Gannon). The use of microwave energy to heat an extractant medium has also been investigated by Ganzler and Salgo, 1987, *Z. Lebensm Unters Forsch* 184: 274–276. In the latter type of application, most of the microwave energy is absorbed by the extractant subsequently resulting in the heating of the extractant; accordingly, very little energy reaches the inner parts of the material to be extracted.

Plant material has been exposed to microwave energy in an air stream to produce headspace-like samples of volatile material as documented by Craveiro et al., 1989, *Flavour and Fragrance Journal* 4: 43–44. No documentation has been compiled in terms of the ability to generate volatiles in a dynamic mode, such as those produced by purge and trap methods, and further no novel apparatus therefor has been set forth.

Canadian Patent No. 987,993 issued to Heitkamp et al., describes a microwave-induced migration of flavours and aromas to the surface of materials, such as tobacco or tea, in the presence of moisture and optionally, a solvent. Ira U.S. Pat. No. 5,002,784, Paré et al., teach that biological materials containing microwave absorbing substances, which are subjected to microwave radiation while in contact with an extractant microwave transparent or partial transparent, results in differential heating of the material to be extracted. The latter effects a disruption of the inner glandular and vascular systems of the material and causes a very rapid selective extraction of a variety of natural products.

SUMMARY OF THE INVENTION

The prior art fails to recognize the usefulness of microwave generation of volatile components containing the same, in the absence of a solvent. Further, the prior art is deficient in terms of any teaching pertaining to the disruption of the equilibrium between the liquid or solid phase containing the volatilizable components and the gaseous phase containing volatilized components or any apparatus capable of effecting the latter.

The present invention is directed to solving these deficiencies and further provides an apparatus which may be associated with other analytical devices, e.g. supercritical fluid and gas chromatography instruments, during the process of generating the volatilizable components.

The need for a general method to generate volatiles both, in a static, and in a dynamic mode, and an apparatus therefor which can be used for a variety of sources or origins, is well recognized. The fragrance, food and environmental industries, in particular, require methods and apparatus that are versatile, relatively inexpensive to operate and that do not involve intricate operations that increase the risks of sample loss and sample contamination.

The extraction industry, the petroleum industry, the health and safety industries associated with emergencies such as those related to chemical spills, in particular, require methods that are versatile with respect to the substance(s), to be selected, relatively inexpensive, simple and safe to operate to minimize the hazards associated with the generation and subsequent handling of substances under that particular state.

In accordance with the present invention, protocols for the generation of volatiles from any liquid or solid matrix can be performed (more easily and with greater efficiency and expediency; such advantages additionally permit less error and less contamination possibilities) when a microwave applicator is used to enhance the volatility of substances that are present in the matrices and, optionally, to disrupt the equilibrium between the liquid or solid phase of the matrix and the resultant gaseous phase from the volatilization of the substances. This procedure may be performed in a closed container so as to bring the chemical composition of the gaseous phase similar or identical to that present originally in the liquid or solid phase, or optionally, to bring one or all of the substances a supercritical state.

One object of the present invention is to provide a process for generating volatiles or supercritical fluid material from any liquid or solid matrix by the steps comprising:

(a) providing volatiles in a subdivided form within a liquid or solid matrix and comprising one or more substances contained in a closed container or the like;

(b) exposing the subdivided material, while within the solid or liquid matrix, to microwave radiation and disrupting the equilibrium between the solid or liquid phase and the gaseous phase in favour of the gaseous phase without physically removing the volatiles, until substantial volatilization of the material has occurred;

(c) subsequently separating the thus created gaseous phase from the solid or liquid phase while still in the same container, or in another container connected thereto, and optionally;

(d) recovering the gaseous phase from the same container or another container connected thereto; or optionally (e) exposing the subdivided material to microwave radiation until sufficient energy has been imparted to bring the material to its supercritical state.

In the above process, and in some cases, the volatiles can be used in applications where their isolation is not required.

Further, where it is desirable to obtain volatiles in the gaseous phase in a relative concentration so as to be similar or substantially identical to that originally present in the solid or liquid phase, the microwave irradiation in step (b) is maintained for a sufficiently long period to effect a disruption of the equilibrium normally present between the gaseous, and the solid or liquid phase, so as to impart energy preferentially to the liquid or solid phase thus resulting in the generation of volatiles in the gaseous phase in the desired proportions.

Preferably, where the desired substances are readily amenable to established analytical protocols, for example, chromatographic separation coupled to an appropriate detector, the gaseous phase arising from the microwave treatment is delivered directly into the selected analytical devices(s) using the apparatus described herein.

Still further, where the desired components are in trace amounts with respect to other substances of relatively different volatility, the invention may be employed in such a manner as to effect the selective and successive volatilization of the various substances. It will be apparent to those skilled in the art that the order in which the components will be volatilized will be determined by the characteristics of the components, namely, the vapour pressure and the dielectric constant.

The microwave dose should be chosen to maximize the volatilization of the desired components, or the conversion to the supercritical state of the desired substance, in a minimal amount of time, without affecting the nature of the components and by selecting appropriate operating parameters based on the nature of the components. The absolute value of the dielectric constant, the heat capacity, the enthalpy of formation, the ionization energy being some of the essential characteristics for this process.

Yet another object of this invention is to provide a method for expressing volatilizable components from a liquid or solid matrix containing the volatilizable components, comprising:

providing a matrix having volatilizable components dispersed therein;

exposing the matrix to microwave energy to effect volatilization of at least one of the volatilizable components; and separating at least one volatilized component from the matrix.

In addition to the foregoing, there is a need for a method of enhancing the volatility of substances present in a matrix having volatilizable components which permits disruption of the equilibrium between the liquid or solid phase of the matrix and the gaseous phase that results from the volatilization, to thereby establish a product which has a chemical composition, in terms of its gaseous phase, which is substantially similar or identical to that present in the original matrix.

A further embodiment of the present invention satiates the aforementioned need and provides, as a further object of the invention, a method of selectively separating volatilizable materials from a liquid or solid matrix containing the volatilizable materials comprising:

providing a matrix selected from a solid or liquid, the matrix having volatilizable materials dispersed therein;

enclosing the matrix within a container, the container having a selectively permeable membrane associated therewith, the membrane adapted to selectively pass at least one of the volatilizable materials when volatilized;

exposing the matrix to microwave energy to effect volatilization of at least one of the volatilizable components in the matrix; and passing at least one volatilized component through the membrane.

As volatility is a physical characteristic specific to a given compound, selectivity of expression for volatilizable compounds contained within a given matrix for selective removal, is desirable. Such removal reduces the likelihood of expressed compounds containing contaminants and results in a generally more efficient expression protocol.

The present invention addresses the favourable technique outlined above and, as yet, another object of the present invention, is to provide a method of sequentially separating volatilizable components from a matrix containing the components each having a different volatility, the improvement comprising the steps of:

providing a matrix having volatilizable materials dispersed therein;

enclosing the matrix within a container, the container having a selectively permeable membrane associated therewith, the membrane adapted to selectively pass through at least one of the volatilizable materials when volatilized;

exposing, in a first exposure step, the matrix to a microwave applicator at a first energy intensity to effect volatilization of at least one of the volatilizable components;

removing at least a first volatilized component;

exposing, in a second exposure step, the matrix to the microwave applicator at a second energy intensity to effect volatilization of at least one of the volatilizable components remaining in the matrix.

In order to facilitate the inventive methods set forth herein, Applicant, in a further aspect of the present invention provides an apparatus suitable for use in the expression of volatilizable compounds comprising:

at least one microwave applicator;

at least one container having an open top and being at least partially transparent to microwaves;

lid or other means such as a closed container for sealing the top of the container; and selectively permeable membrane means associated with said container and adapted to selectively release at least one of the volatilizable compounds when volatilized.

DETAILED DESCRIPTION OF THE PREFERRED EMBODIMENTS

The mechanism of action of this volatile generation process has been investigated using a variety of matrices and conventional sorbents to trap the volatiles evolved. The volatiles were monitored in comparison to those obtained when conventional methods were applied to identical matrices.

These investigations led to the conclusions that the microwave-assisted process proceeds generally as set forth herein. The microwave rays travel freely through the container (selected from those materials partially transparent to microwave rays) and reach the matrix. The matrix is made up of more than one component, each of which possesses characteristic physical properties and, more particularly, dielectric constant and a characteristic vapour pressure. The relative ability exhibited by each of the components to absorb the microwave rays is dependent upon the absolute value of their respective dielectric constant. Generally, components, such as water, possess a large dielectric constant at room temperature and therefore absorb to a great extent the microwave rays. The absorption of the microwave rays subsequently results in the heating of such compounds.

It is possible to control the power of the applied microwave rays so as to ensure an overall heating rate that is constant for each component as the heat so-generated is diffused passively to all of the components throughout the matrix. The rate of volatilization of each component, within a given matrix, is dependent upon the respective vapour pressure thereof. Water, for example, has a lower vapour pressure than benzene, hence benzene will volatilize more rapidly, at a given temperature, than water, thus a net effect of volatilizing the benzene preferentially to the water.

Under conventional steady state heating such as that applied by other technologies, such as conventional headspace analysis, the relative concentration of the volatiles in the gaseous phase is at substantial equilibrium with that in the solid or liquid phase of the matrix and is dependent upon the partial vapour pressure of each component; accordingly, the relative concentration of a given component in the gas phase is not equal to that while in the solid or liquid phase. This poses difficulties during analysis and specifically upon an attempt to quantify a material dispersed in a matrix.

Furthermore, the absolute value of the dielectric constant of a given substance decreases when the substance reaches the gas phase, e.g. liquid water has a dielectric constant of about 80 at 293K while steam, at 373K, has a value of about 1. Hence, almost all of the applied microwave energy is used to selectively heat the liquid or solid phase of the matrix. Moreover, the capacity of a substance to absorb energy while resisting a temperature increase is dependent upon the heat capacity of the substance. As an example, the temperature of 1 gram of water is elevated by only 1K when the same absorbs 1 calorie of energy at 293K.

Having regard to the above, the present invention makes it possible to effectively apply a controlled amount of microwave energy that will selectively heat the liquid phase at a temperature such that the volatiles are maintained in the gaseous phase without volatilizing the non-volatiles. This permits the application of more energy into the matrix to disrupt the phase equilibrium that normally prevails between the gaseous phase and the solid or liquid phase of the matrix as the energy is preferentially absorbed by the liquid, or solid, fraction of the system over the gaseous fraction. Under such conditions, it is possible to generate volatiles into the gas phase so that their relative gaseous concentration is substantially equal to that which they had in the liquid or solid state. This aspect of the invention relates to the generation of volatiles in a purge and trap fashion.

In a further embodiment of the present invention, the gaseous phase can be separated from the liquid or solid phase of the matrix, while enhancing the rate of volatilization, by incorporating the use of an appropriate selectively or semi-permeable membrane that allows the flow of gaseous materials in one direction (away from the matrix) while preventing the flow of liquid or solid materials. The functional use of such membranes will be well-known to those skilled in the art and there are several known types which are used for given bands of selectivity. Preferably, but not exclusively, a membrane that does not allow the passage of water, whether in a liquid or a gaseous state, is appropriate for direct transfer of the volatiles onto an inlet port of an analytical device such as a gas chromatograph. FIG. 1, as described hereinafter, depicts a typical apparatus for this purpose.

In another configuration of this invention, a protocol can be designed to generate supercritical fluids from a variety of materials, water being of particular interest. The dielectric constant of water is about 80 at 293K. At its boiling point, namely 373K, water has a dielectric constant of about 55 whereas steam has a dielectric constant of about 1. Thus, it is possible to heat all of the liquid phase prior to heating the gaseous phase. In a closed container, the temperature and the pressure will rise until the supercritical state is reached. Water exhibits a heat capacity of 1 cal per gram per degree Kelvin at room temperature. Once it reaches the supercritical state, water exhibits a heat capacity that goes to infinity. Thus, by employing the present invention, it is possible to apply enough energy to effect the conversion of liquid water into supercritical water and to maintain it at that state while providing a given level of microwave energy. The resulting supercritical water can be used in other applications, as is the case for supercritical water generated by other technologies. While water is used only as an example, it will be understood that the invention is not limited to water as will be evident to those skilled in the art.

In one preferred configuration of the present invention, an apparatus is provided so that such a membrane is allowed to establish a tight seal in the container enclosing the matrix of interest. The microwave power is applied and as the volatiles generation is effected, the membrane may be moved down toward the matrix so as to reduce the headspace volume above the matrix and the membrane. The semi-permeability of the membrane effects separation as the volatiles are not able to return to the liquid or solid phase. The rate of heating will allow for headspace type of experiments, or if disruption of the equilibrium is effected by applying extra power, then the method will lead to the generation of purge and trap-like experiments. The membrane can also be retracted to its original position thus compressing the volatiles into a smaller volume.

The apparatus, as generally set forth herein, is particularly well-suited for interfacing directly onto the injector port, or other appropriate inlet mechanisms, of an appropriately selected analytical instrument, such as a gas, liquid or supercritical fluid chromatographic instrument. Such an arrangement, by opening of an appropriate valve, allows for on-line transfer of the gaseous volatile materials whereby one can effect a totally automated analytical protocol for headspace or purge and trap types of analysis with a single instrument, an option not available with any other current technology. The separation methods mentioned above were noted only for example purposes and it will be understood that they are not exhaustive nor limiting with respect to other applications of the process and apparatus, to other methods.

Having thus generally described the invention, reference will now be made to the accompanying drawings illustrating preferred embodiments.

The sample used was water contaminated with west Texas sour crude oil at a concentration of 5 parts per million. Headspace analysis carried after a 30-minute incubation period at 358K while the analysis of the volatiles produced by the methodology of the invention was performed after a 30-second irradiation period. All analytical procedures were identical.

Figure 1:
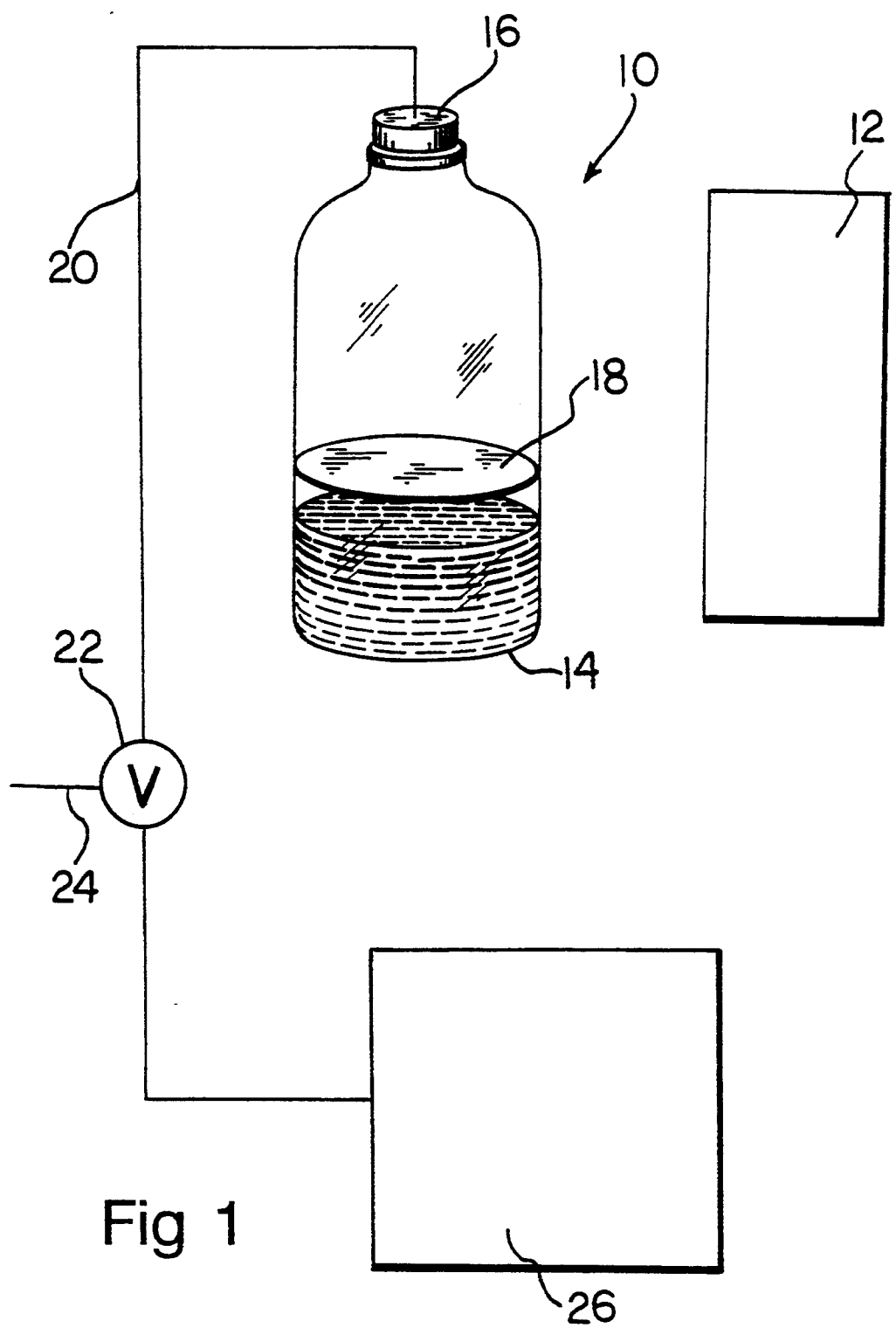
FIG. 1 is a schematic of an apparatus to effect the separation of volatiles, and subsequent direct transfer of said volatiles into another discrete unit.

FIG. 1 illustrates one form of the apparatus. As the volatiles are generated, a mobile semi-permeable or selectively membrane 18 disposed within container 10, moves in response to increasing gaseous pressure and then separates the newly generated gas phase from the liquid or solid phase matrix beneath the membrane 18, generally illustrated in dashed lines. Volatiles passing through membrane 18 exit the container 10 via conduit 20. Volatiles travelling through conduit 20 may be sampled by opening valve 22 for discharge through sampling line 24. The volatiles may additionally be forwarded to analysis means 26, which may comprise any known analysis apparatus, e.g. a gas chromatograph, I.R. spectrophotometer, N.M.R. apparatus, mass spectrometers, U.V. analysis means, etc.

Examples of the invention are provided below wherein microwave radiation-induced volatile generation was used. Disruption of the equilibrium normally present between liquid or solid substances and their gaseous state as described demonstrate improvements in one or more aspects. These aspects include yield, sensitivity, number of volatiles, identity of volatiles, reduced time and production costs (reduced operational costs and reduced capital costs), reduced number of operations and reduced process-related hazards (to humans and to sample integrity), or a combination thereof, over the conventional headspace and purge and trap processes currently used. These examples are illustrative and typical, but are not to be considered exhaustive or limiting.

EXAMPLE 1

As a representative example of headspace analysis, the volatiles from a water sample contaminated with a crude oil were obtained from a conventional headspace sampler and from this invention. Water was contaminated with some west Texas sour crude oil at a concentration of 5 parts per million. Two 10 mL aliquots were transferred into two identical 20 mL vials that were sealed hermetically. The first vial was then subjected to a 30-minute incubation period at 358K on a conventional, commercially available, headspace sampler (Hewlett Packard 19395A). A 1-mL volume of the resulting headspace was injected directly into the injector port of a gas chromatograph (Hewlett Packard 5890 Series II, flame ionization detector) equipped with an appropriate column to effect the separation and the resolution of the volatiles (HP-1, 25 meters, 1 micrometer thickness).

The second vial was subjected to the process taught by this invention, namely by exposure to microwave radiation (2450 MHz, 650 Watts) for 30 seconds. A 1-mL volume of the resulting headspace was injected directly onto the injector port of a gas chromatograph under the same conditions as per the conventional headspace sampler.

Figure 2:
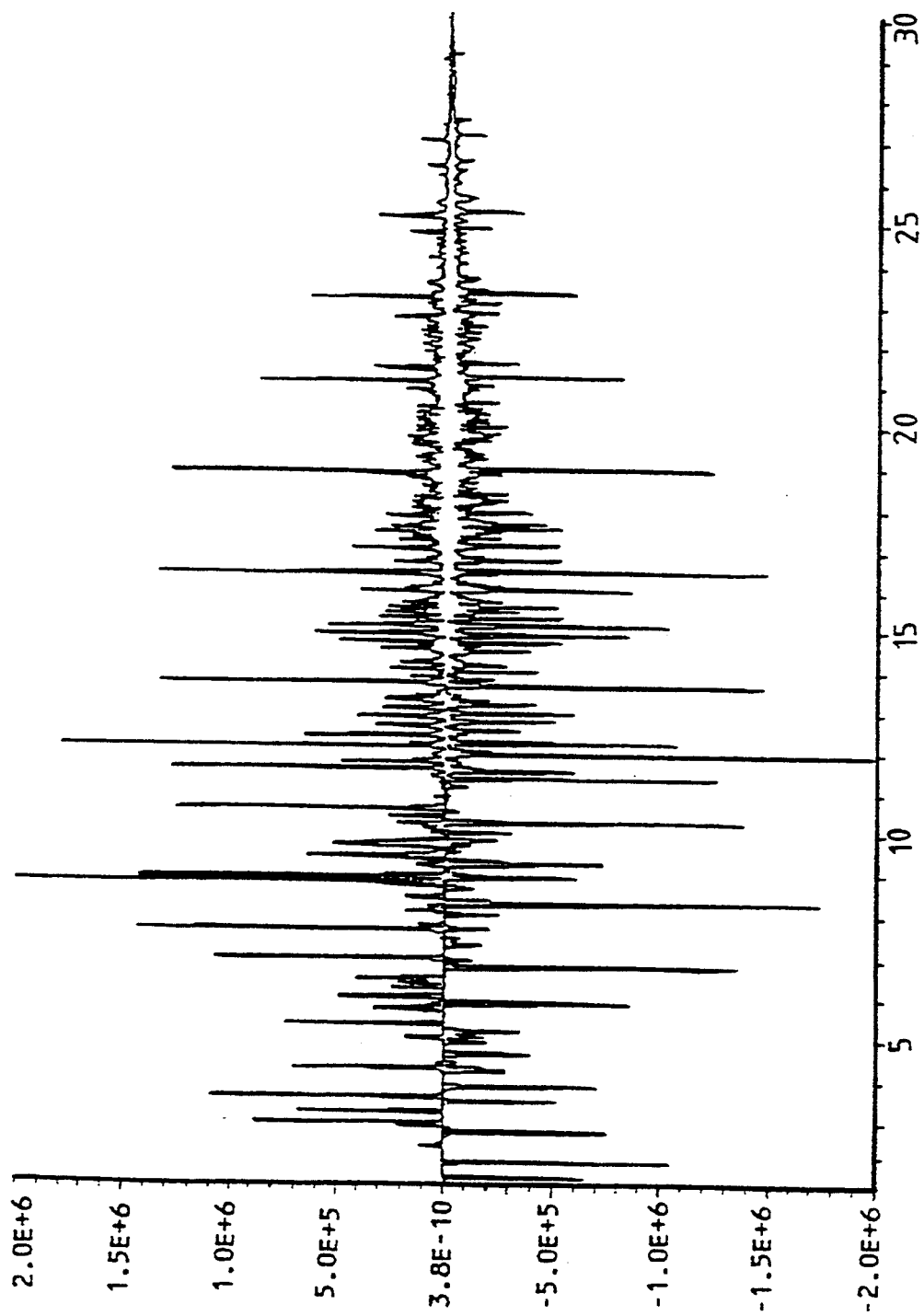
FIG. 2 is a comparison of the gas chromatographs of the volatiles obtained from conventional headspace analysis (top trace—labelled headspace) and from this invention (bottom, inverted trace—labelled MAP).

FIG. 2 shows the two resulting traces recorded under identical conditions, both scales being the same. This example demonstrates that the methodology of the present invention yielded more volatiles, in terms of their overall absolute quantity, in a much reduced sampling time. Furthermore, this example also shows that the use of this invention led to the detection of more components, principally for the more volatile substances, hence an evidence that the excess energy applied to the system was absorbed selectively by the liquid phase over the gaseous phase.

EXAMPLE 2

Fresh sage, of 80% moisture content, obtained from Saint-Jean-sur-Richelieu, Québec, Canada, was chopped coarsely into pieces and subjected to conventional purge and trap analysis as well as to conventional headspace analysis. A portion of the same material was inserted into a container. The container was sealed by a cover through which an orifice had been made. A commercially available sorbent, in an appropriate container, was fitted from the inside of the container to the orifice thus creating an hermetic seal. The container and its contents were then treated by exposure to microwave radiation for 90 seconds so as to severely disrupt the equilibrium that existed between the solid plant material and the gases around it. The sorbent was then eluted and the eluate analyzed by gas chromatography. The results of the analysis evidenced the presence of volatile terpenoids as well as less volatile ones.

A typical analysis contained 4-carene, alpha-thujene, alpha-pinene, camphene, 2-beta-pinene, sabinene, beta-myrcene, 1,8-cineole, beta-phellandrene, alpha-terpinolene, alpha-thujone, beta-thujone, camphor, bornyl acetate, cis-caryophyllene, and alpha-caryophyllene. This analysis compared favourably to the purge and trap analysis, while being superior to the headspace analysis, the latter lacking some of the lesser volatile compounds (sesquiterpenoids).

It will be evident to those skilled in the art that the choice of sorbent is dependent upon the nature of the volatiles of interest (in the present example, a silica sorbent was appropriate). Direct injection of the volatiles without the use of any trap of any kind (cold or sorbent) is possible by the use of this invention because of the short sampling duration and because of the relatively small volume of sampling necessary. Purge and trap would not allow such a direct injection without a cold trap of kind, or of a sorbent. The use of this invention, in this particular example, showed that a purge and trap analysis can be performed more rapidly, with less operations (hence reduced risks of sample loss or sample degradation), at a much reduced cost and with less energy than conventional technology. Again, the use of this invention requires less intricate equipment occupying a much reduced space and obtainable at a much reduced capital cost.

EXAMPLE 3

As a representative example of headspace analysis of a solid matrix, the volatiles from a soil sample contaminated with a crude oil were obtained from a conventional headspace sampler and from this invention. The soil was contaminated with west Texas sour crude oil at a concentration of 4.28 parts per million. Two 1.0 g aliquots were doped with 0.5 mL of water and were transferred into two identical 20 mL hermetically sealed vials. The first vial was subjected to a 30-minute incubation period at 358K on a conventional, commercially available, headspace sampler (Hewlett Packard 19395A). A 1-mL volume of the resulting headspace was injected directly into the injector port of a gas chromatograph (Hewlett Packard 5890 Series II, flame ionization detector) equipped with an appropriate column to effect separation and resolution of the volatiles (HP-1.25 meters, 1 micrometer thickness).

The second vial was subjected to the process according to the present invention, namely by exposure to microwave radiation at a frequency of and a power rating of 650 Watts for 30 seconds. A 1-mL volume of the resulting headspace was injected directly into the gas chromatograph under the same conditions as per the conventional headspace sampler.

The results obtained through this example demonstrate that the sample, when treated according to the present invention, yielded more volatiles, in terms of their overall absolute quantity, in a substantially reduced sampling time and that the nature of the volatiles is exactly identical to that obtained by conventional technology. Furthermore, this example also evidences that the excess energy applied to the system was absorbed selectively by the solid (and small amount of liquid) phase over the gaseous phase.

EXAMPLE 4

This example relates to headspace analysis in the biomedical and forensic fields and indicates usefulness in alcohol detection from an aqueous sample.

The detection of alcohol from an aqueous sample was performed on a conventional headspace sampler and by using the methodology of the present invention. Water was spiked with ethanol at a concentration varying between 0.8 to 80 mg per 100 mL. Two 10 mL aliquots were transferred into two identical 20 mL hermetically sealed vials. The first vial was then subjected to a 30-minute incubation period under conditions set forth in Example 3. A 1-mL volume of the resulting headspace was injected directly into the injector port of a gas chromatograph equipped with an appropriate column to effect the separation and the resolution of the volatiles, these apparatus being those indicated in Example 3.

The second vial was subjected to the process taught by this invention, namely by exposure to microwave radiation (2450 MHz, 650 Watts) for 30 seconds. A 1-mL volume of the resulting headspace was injected into the injector port of a gas chromatograph under the same conditions as per the conventional headspace sampler. An identical experiment was performed by substituting whole cream (35% fat) to water, cream being a most challenging matrix with which to work. The results of this example demonstrate that this invention was more sensitive by a factor of at least 2, required a much reduced sampling time, and provided for the detection of more species (in the case of the cream).

The overall reduction in analysis time evidenced in this example is of extreme importance to forensic and biomedical applications such as the determination of the ethanol content in blood for drivers suspected to be under the influence of alcohol and for the monitoring of dissolved gases in blood of patients undergoing surgery. Again, the example also shows that the use of the invention allowed the excess energy applied to the system to be absorbed selectively by the liquid phase over the gaseous phase. It will also be evident to those skilled in the art that the use of this invention required much less sophisticated equipment and equipment of a substantially reduced size compared to conventional headspace sampler apparatus. Clearly, the present invention affords a much reduced capital cost for the building and design of the conventional apparatus. Finally, the reduced amount of time spent at incubation that the present invention requires, provides for a more cost-effective operation (less energy being used) and a greatly reduced possibility of sample loss, sample degradation and other such impedances.

I claim:

1. A method for expressing volatilizable components from a matrix selected from the group consisting of liquid and solid matrices containing said volatilizable components comprising:
   enclosing a matrix having volatilizable components dispersed therein in a container having a selectively permeable membrane associated therewith, said membrane being adapted to pass selectively at least one volatilized component;
   exposing said matrix to microwave energy to effect volatilization of at least one of said volatilizable components;
   separating at least one volatilized component from said matrix by selectively passing the volatilized component through said membrane as a pressurized gaseous phase; and
   recovering at least one separated component.

2. The method as defined in claim 1, further including the step of enclosing said matrix within a container at least partially transparent to microwaves and positioning said container within a microwave applicator.

3. The method as defined in claim 1, further including the step of movably mounting said membrane to said container.

4. The method as defined in claim 3, further including changing the volume of said container by moving said membrane within said container.

5. The method as defined in claim 4, further including passing separated components into separating means for further separating individual components within said separated components.

6. The method as defined in claim 1, further including condensing separated components from a gas phase to a lower energy phase.

7. The method as defined in claim 1, further including the step of condensing said volatilized components.

8. An apparatus suitable for use in the expression of volatilizable compounds comprising:
   at least one microwave applicator (12);
   at least one container (10) having an open top and being at least partially transparent to microwaves;
   lid means (16) for sealing said top of said container; and
   selectively permeable membrane means (18) associated with said container and adapted to selectively release at least one of said volatilizable compounds when volatilized.

9. The apparatus as defined in claim 8, further including collecting means (26) for collecting volatilized compounds released by said selectively permeable membrane.

10. The apparatus as defined in claim 9, further including sampling means (22,24) for sampling said volatilized compounds.

11. The apparatus as defined in claim 10, further including conduit means (20) extending between and interconnecting said at least one microwave applicator (12), said collection means (26) and said sampling means (22,24).

12. A process for generating volatiles from at least one of a liquid and a solid matrix comprising:
   (a) subdividing a matrix feed material, said matrix containing volatiles in dispersed form;
   (b) exposing the subdivided material, to microwave radiation and disrupting the equilibrium between the matrix phase and the gaseous phase in favour of the gaseous phase without physically removing the volatiles until substantial volatilization of the material and pressurization has occurred due to said radiation;

(c) subsequently separating the so-created gas phase from the matrix phase while still in the same container; and (d) recovering the gaseous phase.

13. The process as defined in claim 12, wherein said matrix feed material comprises a liquid and said gaseous phase comprises a supercritical phase for generating supercritical fluids from said liquid matrix, comprising:

(a) exposing the liquid matrix to microwave radiation and disrupting the equilibrium between the liquid phase and the gaseous phase in favour of the gaseous phase without physically removing the volatiles, until the volatilized material has reached its supercritical state due to said radiation, (b) subsequently separating the so-created supercritical fluid phase from the liquid phase while still in the same container; and (c) recovering the separated supercritical phase.

14. The process as defined in claim 12, wherein at least one of steps (c) or (d) are effected by using a membrane having a property effective to separate a liquid from a gas.

15. The process as defined in claim 12, wherein steps (c) or (d) are effected by using a chemical sorbent agent effective for separating volatiles.

16. The process as defined in claim 12, wherein steps (b), (c) and (d) are repeated in sequence and separate volatiles recovered.

17. The process as defined in claim 12, wherein at least one of steps (c) or (d) are effected by a combination of a membrane, and a chemical sorbent agent effective to separate volatiles.

* * * * *